United States Patent [19]

Lukacsko et al.

[11] Patent Number: 4,757,060

[45] Date of Patent: Jul. 12, 1988

[54] NON-STEROIDAL ANTI-INFLAMMATORY COMPOSITIONS PROTECTED AGAINST GASTROINTESTINAL INJURY WITH A COMBINATION OF CERTAIN $H_1$ AND $H_2$, RECEPTOR BLOCKERS

[75] Inventors: Alison B. Lukacsko, Robbinsville; Randy J. Koslo, East Windsor; Joseph J. Piala, Metuchen, all of N.J.

[73] Assignee: Bristol-Myers Company, New York, N.Y.

[21] Appl. No.: 867,882

[22] Filed: Apr. 29, 1986

Related U.S. Application Data

[63] Continuation-in-part of Ser. No. 836,264, Mar. 4, 1986, abandoned.

[51] Int. Cl.[4] .................. A61K 31/60; A61K 31/62; A61K /615

[52] U.S. Cl. .................................. 514/160; 514/161; 514/162

[58] Field of Search ................ 514/160, 162, 161

[56] References Cited

U.S. PATENT DOCUMENTS 4,401,665 8/1983 Sheinaus et al. ............... 514/162

OTHER PUBLICATIONS

Chem. Abst 93 (1980)–19117K & 94 (1981)–24923V.

Primary Examiner—Stanley J. Friedman
Attorney, Agent, or Firm—Morton S. Simon

[57] ABSTRACT

A pharmaceutical composition and process for administering non-steroidal drugs which are protected against injury to the gastrointestinal tract by a combination of certain $H_1$ and $H_2$ receptor blockers.

17 Claims, No Drawings

NON-STEROIDAL ANTI-INFLAMMATORY COMPOSITIONS PROTECTED AGAINST GASTROINTESTINAL INJURY WITH A COMBINATION OF CERTAIN $H_1$ AND $H_2$, RECEPTOR BLOCKERS

CONTINUING APPLICATION

This application is a continuation in part of Ser. No. 836,264, filed Mar. 4, 1986 and now abandoned.

This invention relates to non-steroidal anti-inflammatory drug (hereinafter referred to as NSAID) compositions containing protectants against NSAID-induced gastrointestinal injury and to processes for administering such composition. More particularly, it concerns compositions and processes of the aforesaid type that employ certain combinations of histamine receptor blockers as the protectants. The compositions of this invention are useful in treating conditions and symptoms that are classically treated by the administration of NSAIDs e.g. headache pain, pain and inflammation associated with arthritis and other systemic diseases, elevated body temperatures etc.

Aspirin and other NSAIDs have long been the most popular drugs for the management of pain, inflammation and fever. However, one of the drawbacks in their use is the gastrointestinal injury and/or bleeding that sometimes accompanies their administration to individuals. This becomes a problem where large and sustained doses of NSAIDs must be given to control the symptoms, as for example, in the case of the management of arthritis.

It has now been found that NSAID-induced gastrointestinal injury can be significantly reduced when a combination of histamine receptor blockers and particularly a combination of $H_1$ and $H_2$ receptor blockers are administered concurrently with the NSAID.

As pointed out in U.S. Pat. No. 4,996,571 $H_1$ and $H_2$ receptor blockers form two well-known classes of pharmacologically active drugs that serve as blocking agents for histamine at $H_1$ and $H_2$ histamine receptor sites, respectively. Histamine receptor sites have been differentiated on the basis of the classes of antihistamines that can serve to block these sites. The fact that a drug is identified as an antihistamine does not necessarily mean that it will be effective in blocking all the known histamine receptor sites but may in fact be selective so that it will act at one site e.g. $H_1$ site but not at another e.g. $H_2$ site.

It has been reported in prior art that $H_2$ receptor blocking agents or antagonists protect against aspirin-induced lesions in certain laboratory animals. One such study is a report in Gastroenterology Vol. 88, No. 5 part 2. p. 1344. It has also been reported that cyproheptadine has been evaluated as a protectant against aspirin induced gastrointestinal injury (Indian J. Med. Res. 1980, 71, p. 926-32). Although the cyproheptadine may have some $H_1$-receptor antagonist properties, it does not act exclusively at the $H_1$ receptor sites but rather acts predominantly at the serotonin receptor sites.

Aside from the above the present invention has further significant distinctions from the teachings in the Indian Journal. For one thing in this reference the aspirin and the cyproheptadine are not coadministered as would be the case in the present invention. Furthermore the treatment in this reference with cyproheptadine is reported as not modifying the gastric acidity. This is contrary to the observations made in connection with the present invention. Moreover, the cyproheptadine was administered by intraperitoneal injection prior to the intragastric administration of the aspirin. In contrast to this the compositions of the present invention lend themselves to oral administration at which time the NSAID and the combination $H_1$ and $H_2$ receptor blockers are coadministered.

As will be pointed out in more detail below it has been found that by employing certain combinations of $H_1$ and $H_2$ histamine receptor blockers as further defined herein that these two act synergistically in their protective effect against NSAID-induced gastrointestinal injury. This was an unexpected result and would not have been anticipated on the basis of the present state of the art.

A number of $H_1$ and $H_2$ receptor blockers are known in the prior art which are useful for the purposes of the present invention. However, not all of the $H_1$ receptors blockers are equally effective in practicing this invention. Those that are useful should also exhibit anticholinergic properties.

By way of illustrating the $H_1$ receptor blockers that may be employed herein mention may be made of the following: ethanolamines (e.g. diphenhydramine or its hydrochloride salt; carbinoxamine or its maleate salt); ethylenediamines (e.g. tripelennamine or its hydrochloride or citrate salts); alkylamines (e.g. chlorpheniramine or its maleate salt, brompheniramine or its maleate salt); piperazines (e.g. hydroxyzine or its hydrochloride or pamoate salts, cyclizine or its hydrochloride or lactate salts, etc. To exemplify the $H_2$ receptor blockers that may be advantageously used in the practice of this invention the following are given: cimetidene, ranitidine, famotidine, etc.

Generally any combination of $H_1$, and $H_2$ receptor blockers as outlined above are useful for the purpose of this invention. Nevertheless certain combinations of $H_1$ and $H_2$ receptor blockers have been found to be particularly efficacious. Thus the combination of chlorpheniramine plus ranitidine, diphenhydramine plus ranitidine, chlorpheniramine plus cimetidine, and diphenhydramine plus cimetidine are the combinations of choice in the present invention.

The $H_1$ and $H_2$ receptors blockers may be used in the form of their bases or in the form of their pharmaceutically acceptable salts. When employed as salts these will usually be acid addition salts wherein the acid portion may be hydrochloric, maleic, ascorbic, citric, pamoic, lactic, tartaric, etc.

The NSAIDs form a well-known class of drugs that are antiinflammatory analgesics. These have the common property of inhibiting the formation of prostagladins which have a protective affect on the gastrointestinal mucosa. See Goodman and Gilman "The Pharmacological Basis for Therapeutics" 7th Edition, p. 678. It is because of this inhibiting effect that the oral administration of drugs of this class tend to result in gastrointestinal injury and/or bleeding and is at least part of the problem that the present invention seeks to reduce or eliminate.

A number of NSAIDs are known in the prior art to which the present invention has application. The most commonly known group are the salicylates of which aspirin is the prime example. A further group of NSAIDs that have utility in connection with the instant invention are the proprionic acid derivatives. Included in this group are ibuprofen, naproxen. A further group of NSAIDs, employable herein are the fenamates and compounds closely related to them structurally. These may be illustrated by such compounds as mefenamic acid, meclofenamate sodium, diclofenac and its sodium salt. Also belonging to the class NSAIDs with which the present invention is concerned are the indole derivatives (e.g. indomethacin); pyrrole alkanoic acid derivatives (e.g. tolmetin); pyrazalone derivatives (e.g. phenylbutazone); oxicams (e.g. piroxicam), etc.

It is contemplated that in the practice of the present invention the NSAID and the histamine receptor blockers will be administered concurrently in a convenient product form. The essential ingredients of such products will be the $H_1$ and $H_2$ receptor blockers and the NSAID. Over and above this these products may also contain other ingredients which will to a large extent depend upon the particular dosage form of the product, e.g. tablets, capsules, powders, suspensions etc.

The quantity of H receptor blocker that will be contained in the composition of this invention may vary somewhat. All that is required is that an effective amount be present so that the $H_1$ receptor blocker can make its contribution as a protectant against NSAID induced gastrointestinal injury.

Similarly the quantity of $H_2$ receptor blocker in the present composition may also vary, Again, all that is required is that amount employed be an effective quantity which will enable the $H_2$ receptor blocker to play its part as protectant.

The NSAID will be contained in the composition of this invention at levels at which it is generally found in therapeutic NSAID compositions intended for oral administration. This will usually be a pharmaceutically acceptable analgesic/ anti-inflammatory dose.

The quantitative relationship of the NSAID and the $H_1$ and $H_2$ receptor blockers contained in the present products may be expressed on the basis of the daily average dose of the ingredient, e.g mg/kg. of body weight/day. In this case the average daily dose for the ingredients will have the values in the range set forth in the following table:

| Ingredient | General Range | Preferred Range |
|---|---|---|
| NSAID | about 10/mg/kg/day to about 100 mg/kg/day | about 15 mg/kg/day to about 75 mg/kg/day |
| $H_1$ Receptor Blocker | about 2.5 ug/kg/day to about 500 mg/kg/day | about 100 ug/kg/day to about 50 mg/kg/day |
| $H_2$ Receptor Blocker | about 10 ug/kg/day to about 1 g/kg/day | about 0.010 mg/kg/day to about 10 mg/kg/day |

The unit dosage forms for the present products will be formulated for convenient oral administration. Each such unit will generally contain from about 200 mg to about 600 mg of NSAID, from about 0.1 mg to about 70 mg of $H_1$ receptor blocker and from 0.5 mg to about 350 mg of $H_2$ receptor blocker. In formulating these products pharmaceutically acceptable doses of the aforesaid ingredients within the ranges set out above will be employed.

Depending upon the dosage form employed the products of this invention may also contain other adjuvants that may be useful in formulating or administering the particular dosage form. Thus, for example, when administered as a tablet the products of this invention may also contain lubricants, excipients, binding agents, disintegrating agents, flavoring agents, etc. In addition these products may also contain other pharmaceutically active ingredients such as: decongestants, analgesic adjuvants, antihistamines, expectorants, antitussives, diuretics, other analgesics, other anti-inflammatory agents, antipyretics, antirheumatics, anti-oxidants, vasodilators, smooth muscle relaxants, skeletal muscle relaxants, bronchodilators, vitamins, trace minerals, amino acids and biological peptides.

The products of this invention may take a variety of forms. As indicated above they may assume the form of tablets. However, the NSAID and the $H_1$ and $H_2$ receptor blockers may also be in powdered or granular form contained in edible capsules such as gelatin capsules. The present products may also take the form of suspensions or solutions of the above ingredients in a suitable liquid medium or as powders packaged in suitable paper envelopes.

The following Examples are given to further illustrate the present invention. It is to be understood, however, that this invention is not limited thereto.

EXAMPLE 1

| | |
|---|---|
| Aspirin | 325 mg |
| Ranitidine hydrochloride | 3.33 mg |
| Chlorpheniramine maleate | 3.33 mg |

The above ingredients are mixed in powdered or granular form and loaded into gelatin capsules.

EXAMPLE 2

| | |
|---|---|
| Aspirin | 325 mg |
| Cimetidine hydrochloride | 16.67 mg |
| Chlorpheniramine maleate | 3.33 mg |

Prepared as described in Example 1.

EXAMPLE 3

| | |
|---|---|
| Aspirin | 325 mg |
| Cimetidine hydrochloride | 3.33 mg |
| Diphenhyramine hydrochloride | 16.67 mg |

Prepared as described in Example 1.

The following experiments were carried out to test the effectiveness of the combination of $H_1$ and $H_2$ receptor blockers in protecting the stomach against NSAID-induced gastrointestinal injury and to compare any protection afforded by the individual $H_1$ and $H_2$ receptor blockers. In these studies the $H_1$ and $H_2$ receptor blockers are used in the form of the following acid salts: ranitidine HCl, diphenhydramine HCl, chloropheniramine maleate, cimetidine HCl. A standard dose of 975 mg of aspirin is administered orally to dogs along with, respectively, treatment (a) through (h) as indicated below. The stomach lining of the dogs are examined endoscopically and rated as to the degree of injury. The results are given in the table following the description of the methodology.

| treatment | cimetidine 50 mg | ranitidine 10 mg | diphenhydramine 50 mg | chlorpheniramine 10 mg |
|---|---|---|---|---|
| a | x | | | |
| b | | x | | |

-continued

| treatment | cimetidine 50 mg | ranitidine 10 mg | diphenhydramine 50 mg | chlorpheniramine 10 mg |
|---|---|---|---|---|
| c |  |  | x |  |
| d |  |  |  | x |
| e |  | x | x |  |
| f | x |  | x |  |
| g |  | x |  | x |

All test formulations are prepared on the day of the tests. The capsules are placed in the back of the dog's throat. A stomach catheter with attached funnel is positioned in the dog's stomach and 50 ml. of deionized water is administered.

Healthy adult beagle dogs of either sex are selected for testing. Dogs are housed individually in stainless steel cages with grid floors to allow excreta to pass through. Room temperature in the holding rooms and test laboratories is maintained between 65° F. and 85° F. and relative humidity between 30% and 80%. Room lights remain on from 6:00 AM to 4:00 PM.

Each dog is trained to stand in a stanchion with sling support and to accept a bit tied in its mouth. A gastroscope is then passed through the bit into the dog's stomach. This training requires ten days to two weeks in most dogs.

To determine whether a dog is suitable for test purposes, its stomach is examined for a normal mucosa, and its gastric responsiveness to NSAID is evaluated (as under Test procedure). An acceptable gastric irritation score in the antrum must be 5 or greater, 2 hours after dosage.

Food is withheld from test dogs for 24 hrs. before the test and during the test and water is allowed ad lib. The dogs are moved into a holding area away from the kennel. Fasted dogs of either sex are examined gastroscopically to ensure that their stomachs have normal healthy mucosal linings. The dogs are dosed orally with test formulations, which are flushed into their stomachs with 5 ml. of deionized water. They are then re-examined two and four hours later for gastric petechiae and signs of bleeding according to the following scale:
0=uniform, pale to dark pink mucosa
1=darker pink or blotchy mucosa
2=petechias and/or light red streaks
3=few small lesions
4=many or connected small lesions (striations)
5=few large lesions
6=many large lesions
7=massive hemorrhagic damage
Severity of injury for each treatment and at each time is calculated as the mean gastric irritation score.

In addition to the endoscopic observation of the gastric mucosa of each dog a qualitative description of gastric fluid is recorded and a pH measurement is made of the gastric fluid. All of these are done 2 hours after administration of the test product.

A base line is established by measuring the various parameters after the administration of 975 mg of aspirin by itself. The resting stomach has an irritation score of 0 and a pH of 5 to 5.5. Aspirin alone produces injury which scores at approximately 5.6 after 2 hours and the gastric pH at this time is about 3.1. After 4 hours these values are 4.0 for the irritation factor and the pH is about 4.7. This indicates that a certain amount of healing takes place between the 2nd and 4th hour after administration.

The results of these tests with respect to the two hour injury daa are summarized in the following table below:

| Test Composition | 2 Hr. Score Injury | pH |
|---|---|---|
| aspirin (975 mg) | 5.6 | 3.1 |
| aspirin (975 mg) + ranitidine HCl (10 mg) | 3.5 | 5.3 |
| aspirin (975 mg) + chlorpheniramine maleate (10 mg) | 4.0 | 4.4 |
| aspirin (975 mg) + cimetidine HCl (50 mg) | 2.4 | 5.6 |
| aspirin (975 mg) + diphenhydramine HCl (50 mg) | 4.0 | 3.6 |
| aspirin (975 mg) + ranitidine HCl (10 mg) + diphenhydramine HCl (50 mg) | 0.6 | 5.4 |
| aspirin (975 mg) + ranitidine HCl (10 mg) + chlorpheniramine maleate (10 mg) | 1.6 | 4.7 |
| aspirin (975 mg) + cimetidine HCl (50 mg) + diphenhydramine HCl (50 mg) | 1.0 | 7.0 |

An examination of these data shows that singificantly more, synergistic protection is obtained when a combination of an $H_1$ and $H_2$ receptor blocker is employed together with aspirin as compared with the cases in which $H_1$ or $H_2$ receptor blocker, respectively, is issued alone.

We claim:
1. A NSAID composition having reduced potential for NSAID induced gastrointestinal injury comprising
   (a) an analgesic or antiinflammatory amount of a NSAID selected from the group consisting of aspirin and pharmaceutically acceptable salts of aspirin; and
   (b) a protective amount of:
      (i) an $H_1$ receptor blocker selected from the group consisting of diphenhydramine and pharmaceutically acceptable salts of diphenhydramine; and
      (ii) an $H_2$ receptor blocker selected from the group consisting of cimetidine, ranitidine, famotidine and pharmaceutically acceptable salts thereof; said NSAID being present in the composition in an amount of from about 10 mg to about 100 mg per kg per day, based on the weight of a subject to whom the composition is being administered; said $H_1$ receptor blocker being present in the composition in an amount of from about 2.5 g to about 500 mg per kg per day, based on the weight of a subject to whom the composition is being administered; and said $H_2$ receptor being present in the composition in an amount of from about 10 g to about 1 g per kg per day, based on the weight of a subject to whom the composition is being administered.

2. The composition according to claim 1, wherein the $H_2$ receptor blocker is ranitidine or a pharmaceutically acceptable salt of ranitidine.

3. The composition according to claim 1, wherein the $H_2$ receptor blocker is cimetidine or a pharmaceutically acceptable salt of cimetidine.

4. The composition according to claim 1, wherein the $H_2$ receptor blocker is famotidine or a pharmaceutically acceptable salt of famotidine.

5. The composition according to claim 1, wherein the NSAID is present in an amount of from abut 200 mg to about 600 mg; the $H_1$ receptor blocker is present in an amount of from about 0.1 mg to about 70 mg; and the $H_2$ receptor blocker is present in an amount of from about 0.5 mg to about 350 mg.

6. The composition according to claim 2, wherein the NSAID is 975 mg of aspirin, the $H_1$ receptor blocker is 50 mg of diphenhydramine HCl, and the $H_2$ receptor blocker is 10 mg of ranitidine HCl.

7. The composition according to claim 3, wherein the NSAID is 975 mg of aspirin, the $H_1$ receptor blocker is 50 mg of diphenhydramine HCl and the $H_2$ receptor blocker is 50 mg of cimetidine HCl.

8. A process for reducing the potential of aspirin or of a pharmaceutically acceptable salt of aspirin, to induce gastrointestinal injury in a subject which comprises administering to said subject, based on the weight of the subject,
   (a) from about 10 mg to about 100 mg per kg per day of an NSAID selected from the group consisting of aspirin and pharmaceutically acceptable salts of aspirin;
   (b) from about 2.5 μg to about 500 mg per kg per day of an $H_1$ receptor blocker selected from the group consisting of diphenydramine and pharmaceutically acceptable salts of diphenydramine; and
   (c) from about 10 μg to about 1 g per kg per day of an $H_2$ receptor binder selected from the group consisting of cimetidine, ranitidine, famotidine, and pharmaceutically acceptable salts thereof.

9. The process according to claim 8, wherein the NSAID, the $H_1$ receptor blocker and the $H_2$ receptor blocker are administered orally.

10. The process according to claim 9, wherein the NSAID, the $H_1$ receptor blocker, and the $H_2$ receptor blocker are administered concomitantly.

11. The process according to claim 8, wherein the $H_2$ receptor blocker is ranitidine or a pharmaceutically acceptable salt of ranitidine.

12. The process according to claim 8, wherein the $H_2$ receptor blocker is cimetidine or a pharmaceutically acceptale salt of cimetidine.

13. The process according to claim 8, wherein the $H_2$ receptor blocker is famotidine or a pharmaceutically acceptable salt of famotidine.

14. The process according to claim 8, wherein the NSAID and the $H_1$ and $H_2$ receptor blockers are administered in a unit dosage form containing from about 200 mg to about 600 mg of NSAID, from about 0.1 mg to about 70 mg of $H_1$ receptor blocker and from about 0.5 mg to about 350 mg of $H_2$ receptor blocker.

15. The process according to claim 8, wherein the NSAID and the $H_1$ and $H_2$ receptor blockers are administered to a subject in a daily average done based on the weight of the subject, of from about 10 mg per kg per day to about 100 mg per kg per day of NSAID, from about 2.5 g per kg per day to about 500 mg per kg per day of $H_1$ receptor blocker, and from about 10 g per keg per day to about 1 gm per kg per day of $H_2$ receptor blocker.

16. The process according to claim 11, wherein 975 mg of aspirin, 50 mg of diphenhydramine HCl and 10 mg of ranitidine HCl are administered.

17. The process according to claim 12, wherein 975 mg of aspirin, 50 mg of diphenhydramine HCl and 50 mg of cimetidine HCl are administered.

* * * * *

UNITED STATES PATENT AND TRADEMARK OFFICE
CERTIFICATE OF CORRECTION

PATENT NO. : 4,757,060

DATED : July 12, 1988

INVENTOR(S) : Alison B. Lukacsko, Randy J. Koslo, Joseph J. Piala

It is certified that error appears in the above-identified patent and that said Letters Patent is hereby corrected as shown below:

In Column 6, at line 48, change "2.5 g" to --2.5 µg-- and, at line 52, change "10 g" to --10 µg--.

In Column 8, at line 24, change "2.5 g" to --2.5 µg-- and, at line 25, change "10 g" to --10 µg-- and, on the same line, change "keg" to --kg--.

Signed and Sealed this

Fifth Day of May, 1992

Attest:

DOUGLAS B. COMER

Attesting Officer

Acting Commissioner of Patents and Trademarks